United States Patent [19]
Hilston et al.

[11] Patent Number: 5,720,739
[45] Date of Patent: Feb. 24, 1998

[54] CONTROLLED ADHESION STRIP

[75] Inventors: Michael D. Hilston; Thanh V. Nguyen, both of Painesville; Richard A. Huskey, Mentor, all of Ohio

[73] Assignee: Avery Dennison Corporation, Pasadena, Calif.

[21] Appl. No.: 550,279

[22] Filed: Oct. 30, 1995

Related U.S. Application Data

[63] Continuation of Ser. No. 415,154, Mar. 31, 1995, abandoned, which is a continuation of Ser. No. 205,707, Mar. 3, 1994, abandoned.

[51] Int. Cl.$^6$ .................................................. A61F 13/15
[52] U.S. Cl. .................. 604/390; 428/195; 428/202; 428/352; 428/354; 428/483; 428/520; 428/522; 604/389
[58] Field of Search ................. 428/195, 202, 428/352, 354, 483, 520, 522; 604/389, 390

[56] References Cited

U.S. PATENT DOCUMENTS

| | | | |
|---|---|---|---|
| 2,532,011 | 11/1950 | Dahlquist et al. | 154/53.5 |
| 4,472,480 | 9/1984 | Olson | 428/332 |
| 4,530,879 | 7/1985 | Drahnak | 428/352 |
| 4,643,730 | 2/1987 | Chen et al. | 604/390 |
| 4,710,190 | 12/1987 | Wood et al. | 604/389 |
| 5,026,446 | 6/1991 | Johnston et al. | 156/153 |
| 5,106,383 | 4/1992 | Mulder et al. | 604/389 |
| 5,145,718 | 9/1992 | Pedginski et al. | 427/171 |

FOREIGN PATENT DOCUMENTS

2129689  5/1984  United Kingdom.

OTHER PUBLICATIONS

Oraby et al., "Elastomeric Electron Beam–Cured Coatings: Structure-Property Relationships, I. Oligomer Structure" Jour. of App. Sci, vol. 23, 3227–3242 (1979), John Wiley & Sons.

Written Opinion Under PCT Rule 66 mailed Dec. 8, 1995 for PCT International Application PCT/US95/02449.

*Primary Examiner*—D. S. Nakarani
*Attorney, Agent, or Firm*—Renner, Otto, Boisselle & Sklar, P.L.L.

[57] ABSTRACT

An adhesive strip is described which comprises
- (A) a polymer backing sheet material;
- (B) a controlled adhesion coating on one surface of said sheet material, said coating comprising a radiation-cured mixture comprising
  - (B-1) a major amount of at least one acrylate oligomer selected from amine acrylate oligomers, epoxy acrylate oligomers, urethane acrylate oligomers and acrylic acrylate oligomers, and
  - (B-2) a minor amount of at least one monomer selected from monofunctional acrylate monomers and polyfunctional acrylate monomers, and
- (C) an adhesive on the other surface of said sheet material. Articles such as disposable diapers also are described which utilize the strip as a target strip or landing zone for pressure-sensitive adhesive fastening tabs when the diaper is fastened around the body.

14 Claims, 1 Drawing Sheet

CONTROLLED ADHESION STRIP

This is a continuation of application Ser. No. 08/415,154 filed on Mar. 31, 1995, now abandoned, which is a continuation of application Ser. No. 08/205,707 filed on Mar. 3, 1994, now abandoned.

TECHNICAL FIELD

This invention relates to adhesive strips. More particularly, the invention relates to multi-layer strips suitable for use as reinforcing target strips on articles such as diapers, and diapers having a reinforced area for receiving adhesive fastening tapes.

BACKGROUND OF THE INVENTION

The present invention relates to adhesive strips, and more particularly, to the art of disposable diapers that have a reinforced fastening area, i.e., the area of the diaper to which an adhesive tape is pressed to fasten the diaper around an infant or other person. The adhesive fastening tape is formulated to be sufficiently tacky to hold the tape securely in place while in storage, and to insure against undesirable release once a diaper is put on an infant.

Disposable garments such as diapers generally comprise a liquid permeable inner layer, a liquid impermeable out layer or back sheet and an absorbent batt secured between the liner and backing sheet. The inner liner may be any soft, flexible, porous sheet through which fluid may pass, and the inner liner may be comprised of a non-woven web or sheet of polyolefin fibers such as polypropylene, wet strength tissue paper, a spun-woven filament sheet, etc. The liquid impermeable outer sheet may be comprised of a thin web or sheet of polyolefin or plastic film material such as polyethylene, polypropylene, polyvinylchloride, etc. The absorbent batt may be comprised of any suitable absorbent material. Typically, the batt is comprised of a cellulosic material, such as air-formed batt of wood pulp fiber commonly known as "fluff."

The fastener tape closure systems used in disposable articles such as diapers include a pressure-sensitive adhesive tape tab attached at selected locations of the article such as at each of the two corners located at one end of the diaper. The unattached portions of the adhesive fastener tape tabs are configured to adhesively engage with the outer layer of the article at locations on other portions of the article. For example, the attachment zones for the fastening tape tabs are typically located at the opposite end of a diaper.

Releasable and refastenable tape tabs and tape tab closure systems are desired to allow the articles such as a diaper to be removed and refitted. For example, it often is desired to loosen or remove the diaper to determine if it is wet or to remove the diaper to bathe the infant. If the diaper has not been soiled, it can be reused.

The adhesive tape tabs employed to fasten a diaper in a closed position, however, have to be fairly aggressive to provide an adhesive bond adequate to secure the waist portions of the diaper together. The adhesive bond strength generally is greater than the tensile strength and tear resistance of the materials comprising the impermeable outer layer or backing sheet. As a result, when the fastening tape tab is released or peeled from the diaper, the outer layer or backing sheet may tear away from the diaper whereby the diaper cannot be reused because the fastening tape cannot be reused. This problem occurs in part because the outer layer generally is a thin film of polymer material to reduce the weight and the cost of the disposable article. Therefore, when attempts are made to remove or reposition the adhesive fastening tape tab, the forces applied are sufficient to tear the outer polymer film of the diaper.

Various attempts have been made to provide releasable and reusable fastening tapes and tape closure systems. For example, attempts have been made to modify the aggressiveness or bonding strength of the adhesive used to form the adhesive tape. Another solution to this problem would be to use thicker, stronger and more tear-resistant materials as the outer layer, but this solution significantly raises the cost of the article increase the weight of the article and generally decreases softness and flexibility of the garment.

Proposals have been made to resolve these problems by reinforcing the area of the article which receives the adhesive fastening or closure tape. This area of the diaper to which the fastening tape is bonded when the diaper is applied is referred to in the industry as the "target zone" or "landing zone." In U.S. Pat. No. 4,643,730, the landing zone of the outer layer of a diaper is reinforced by coating that area of the outer layer (i.e., the area ultimately receiving the adhesive closure tape) with a layer of material that is curable by high-energy radiation. The cured coating forms a reinforcement layer affixed to the outer layer of the article. The radiation-curable compositions include at least one compound selected from the group consisting of urethane acrylate acrylic oligomers, acrylated acrylic oligomers and epoxy acrylate acrylic oligomers. The compositions also may contain monofunctional acrylate monomers, difunctional acrylate monomers, acrylic monomers and trifunctional acrylate monomers.

U.K. Patent 2,129,689 describes diapers which are provided with a non-elastic plastic strip in the region for fastening the tape tabs. The plastic strips are typically polyester, polyethylene, or polypropylene having a tear strength greater than the outer layer of the diaper. Since the plastic strip is non-elastic, there is no stretching when the fastening tab is removed from the strip.

U.S. Pat. No. 4,710,190 (Wood et al) discloses the use of a bilayer film as a reinforcing film for the outer layer of disposable diapers. The bilayer film comprises a reinforcing layer and a room temperature non-tacky bonding layer which will soften and bond at comparatively low temperatures of less than about 115°–120° C. Because the adhesive is non-tacky at room temperature (non-blocking), the bilayer film is windable into a storage roll in which under normal storage conditions of about 50°–60° C. or less, the overlying potions of the bilayer film do not become adhered together so as to resist uniform low-force unwinding. When applied to a substrate (such as a diaper) and subjected to heat and pressure, the bilayer film is bonded to the substrate in a peel-resistant manner so that the adhesive fastening tape tabs may be strongly adhered to the fastening area by simple hand pressure and held to the diaper without cohesive or other failure of the reinforced portion of the diaper. In addition, the patentees suggest that the fastening tape tabs may be removed and reapplied without distortion or tearing of the outer layer of the diaper.

U.S. Pat. No. 5,026,446 (Johnston et al) describes disposable diapers having target strips wherein the target strips are cut from a pressure-sensitive adhesive tape. The tape has a backing that has a low-adhesion backsize coating on its non-adhesive face, and at least part, but not all, of the low-adhesion backsize coating is removed with an abrasive to improve the adhesion thereof to pressure-sensitive adhesive tape tabs. A number of low-adhesion backsize coatings are described in Col. 2, and these include urethane backsizes as described in U.S. Pat. No. 2,532,011; fluorochemical backsizes such as fluorochemical acrylates as described in U.S. Pat. No. 4,472,480, and ultraviolet light curable silicone backsizes such as described in U.S. Pat. No. 4,530,879. At least 20% of the backsize coating is removed by the abrasive strip.

U.S. Pat. No. 5,106,383 (Mulder et al) describes disposable articles such as diapers containing a closure system comprising a film substrate having a target strip and a fastening tape. The target strip comprises a backing film having a first pressure-sensitive adhesive on one face thereof adhered to the film substrate, and on the other face thereof, a hydrophobic polyvinyl carbamate release coating. The fastening tape tabs have a pressure-sensitive adhesive on one face thereof for adhesion to the target strip. The target strip release coating is subjected to ionizing plasma treatment such that the fastening tape has an increase in adhesion to the target strip of at least about 50% over untreated target strips.

SUMMARY OF THE INVENTION

An adhesive strip is described which comprises (A) a polymer backing sheet material;

(B) a controlled adhesion coating on one surface of said sheet material, said coating comprising a radiation-cured mixture comprising (B-1) a major amount of at least one acrylate oligomer selected from amine acrylate oligomers, epoxy acrylate oligomers, urethane acrylate oligomers and acrylic acrylate oligomers, and (B-2) a minor amount of at least one monomer selected from monofunctional acrylate monomers and polyfunctional acrylate monomers, and (C) an adhesive on the other surface of said sheet material. Articles such as disposable diapers also are described which utilize the strip as a target strip or landing zone for pressure-sensitive adhesive fastening tabs when the diaper is fastened around the body.

DETAILED DESCRIPTION OF THE INVENTION

Figure 1:
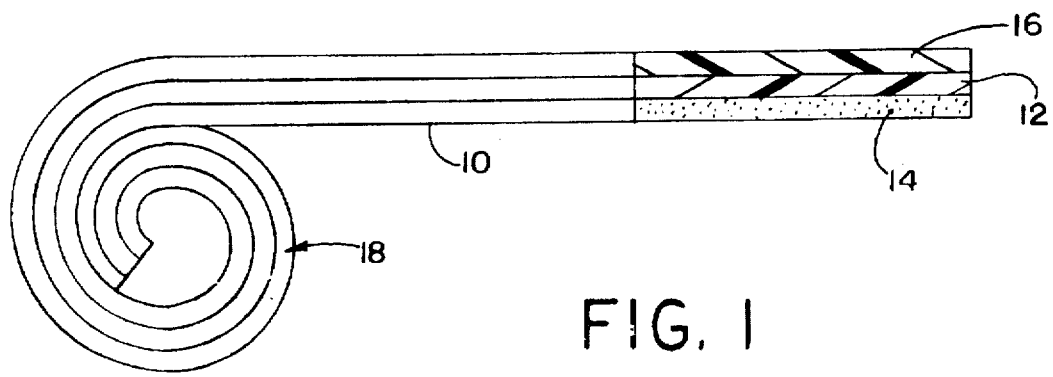
FIG. 1 is a perspective and cross-sectional view of a roll of the adhesive strip of the invention.

In one embodiment, the present invention is an adhesive strip comprising (A) a polymeric backing sheet material;

(B) a controlled adhesion coating on one surface of said sheet material; and (C) an adhesive on the other surface of said sheet material.

A variety of materials can be used to provide the polymer backing sheet material of the strips of this invention. Particularly when the strip is to be used to reinforce another material, the backing sheet material should have a high strength which is typically higher than the material which is to be reinforced by the strip. The strength may be controlled through the use of high strength materials and/or through the use of greater thicknesses of materials. Typically, the polymer backing sheet material will comprise high-strength thermoplastic materials such as polyesters or polyolefins which may be cast or oriented. Examples of polyester materials include polyethylene terephthalate and polybutylene terephthalate films. Examples of polyolefins include polyethylene, polypropylene, and copolymers of ethylene and polypropylene. In one embodiment, the polymer backing sheet comprises a biaxially oriented polypropylene film and in another embodiment, biaxially oriented polyethylene terephthalate film. The polymer backing sheet material used in the strips of the invention may have a matte or glossy finish and/or a smooth or irregular surface (e.g., embossed). Typically the thickness of the polymer backing sheet is between about 10 and 75 micrometers, and more often from about 15 to about 50 micrometers.

A controlled adhesion coating (B) is present on one surface of the polymeric backing sheet material (A) of the reinforcing strip to control (improve) the adhesion of, for example, pressure-sensitive adhesive fastening tape tabs to the target strip while allowing the tape tabs to be easily removed and refastened when desired. The adhesion characteristics can be controlled (adjusted) by varying the components and amount of components in the curable composition used to form the "controlled adhesion" coating (B). The controlled adhesion coating generally comprises a radiation-cured mixture comprising (B-1) a major amount of at least one oligomer selected from amine acrylate oligomers, epoxy acrylate oligomers, urethane acrylate oligomers and acrylic acrylate oligomers, and (B-2) a minor amount of at least one monomer selected from monofunctional acrylate monomers and polyfunctional acrylate monomers.

Higher adhesive strength is obtained when the mixture contains a lesser or no amount of the monofunctional acrylate monomer, and the adhesive strength can be reduced as desired by including increasing amounts of the monofunctional acrylate monomer.

The oligomers (B-1) comprise reactive molecules with a "backbone" structure. The molecular weights of the oligomers utilized in the controlled adhesion compositions may be selected to provide desirable properties such as increased flexibility, hardness, etc., in the cured coating. For example, a higher molecular weight urethane acrylate oligomer provides greater flexibility in the cured coating. The oligomers used in the present invention will have molecular weights in the range of from about 500 to about 6000 as described more fully below.

The amine acrylate oligomers can be obtained by reaction of an organopolyamino compound with acrylic acid, methacrylic or ethacrylic acid. Thus, the amine acrylate oligomers contain at least two acrylyl, methacrylyl or ethacrylyl groups which form a network upon polymerization (curing). The acrylated organic polyamino oligomers useful in the controlled adhesion coating include compounds represented by the general formula

$$R\text{--}(\text{--}C(O)\text{--}C(X)\text{=}CH_2)_n \qquad (I)$$

wherein R is derived from a polyamine, X is hydrogen, or a methyl or ethyl group, preferably hydrogen or methyl, and n is an integer of at least 2 and is preferably 2, 3 or 4. The polyamines may be monomeric compounds such as ethylenedime, 1,3-propanediamine, 1,4-butanediamine, 1,6-hexanediamine, dimethylenetriamine, dipropylenetriamine, triethylenetetramine, etc. The polyamines also may be oligomeric compounds such as dimeric, trimeric or tetrameric polyamino compounds. The acrylated and methacrylated organic polyamino oligomers used in the controlled adhesion coating and generally represented by the above Formula I may be prepared by techniques well known to those skilled in the art such as by the reaction of a polyamine compound with acrylic acid or methacrylic acid in amounts to provide the desired di-, tri, tetra-, or polyacrylated product. The molecular weights of the acrylated and methacrylated polyamine oligomers may be as high as 2000 and are generally below about 1200. In one embodiment, the molecular weight of the acrylated and methacrylated polyamines is within the range of from about 500 to about 1000. It is preferred that these acrylated and methacrylated polyamine oligomers are liquids so that they may be readily blended with the acrylated polyhydroxy compounds utilized in the controlled adhesion coating. In general, the acrylated and methacrylated polyamine oligomers may have viscosities at 25° C. of from about 2 to about 2500 cps., preferably, from about 50 to about 2000 cps., and more preferably between about 400 and about 2000 cps.

Specific examples of acrylated or methacrylated organic polyamino oligomers include, for example, N,N'-diacrylylethylenediamine, N,N'-diacrylyl-1,3-propanediamine, N,N'-dimethacrylyl-1,6-hexanediamine, etc. Useful acrylated and methacrylated polyamino oligomers are available commercially. An example of a commercially available acrylated amine product is Novacure®7100, an acrylated amine oligomer available from UCB Radcure, Atlanta, Ga. This acrylate functional oligomeric amine is a liquid having a viscosity in the range of 500–1500 cps at 25° C. and theoretical molecular weight of 800, and the oligomer contains less than 10% of hexanedioldiacrylate added by the manufacturer as a viscosity control agent.

The acrylate oligomer utilized in the controlled adhesion coatings of the present invention also may be a urethane acrylate oligomer whose structure may be generally characterized as follows:

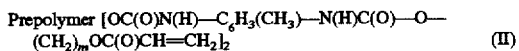
Prepolymer [OC(O)N(H)—C$_6$H$_3$(CH$_3$)—N(H)C(O)—O—(CH$_2$)$_m$OC(O)CH=CH$_2$]$_2$ (II)

wherein m is an integer from 1 to about 10, generally from 1 to 4. In one embodiment, the prepolymer is illustrated by the formula

—(EG—ADA)$_n$—EG—TDI— (IIA)

wherein EG is ethylene glycol, ADA is adipic acid, and TDI is toluene diisocyanate. In one example of the above oligomers, the molecular weight is between about 1000 and 6000 (by varying the values of m and n). As the molecular weight increases, (i.e., the values of m and n increase) the molecular chain length between the two end acrylate groups increases. An increase in the lower molecular weight range generally is achieved by an increase in the soft polyester segment (increasing m) up to about a molecular weight of about 4800. Further increase in the molecular weight (to about 6000) is achieved primarily by increasing the urethane segment (increasing value of n). Urethane acrylic oligomers and oligomer/monomer mixtures are described by W. Oraby and W. K. Walsh, "Elastomeric Electron Beam-Cured Coatings: Structure-Property Relationships. I. Oligomer Structure," Journal of Applied Polymer Science, Vol. 23, pages 3227–3242 (1979).

Suitable urethane acrylate oligomers are commercially available under such designations as Chempol 19-4827 which is available from Radcure, Inc., Port Washington, Wis. This oligomer is a 100% solids, general purpose acrylated aromatic urethane which may be cured by exposure of either ultraviolet light or electron beam radiation. The molecular weight of this oligomer is about 1500. Urethane acrylate oligomers also are available from Morton Thiokol under the designations Uvithane 782 and Uvithane 783.

The acrylate oligomers useful in the present invention also may be epoxy acrylate oligomers such as the following oligomer represented by Formula III

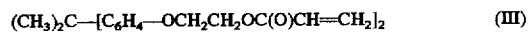
(CH$_3$)$_2$C—[C$_6$H$_4$—OCH$_2$CH$_2$OC(O)CH=CH$_2$]$_2$ (III)

and the acrylic acrylate oligomers may be represented by the following Formula IV

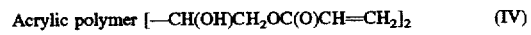
Acrylic polymer [—CH(OH)CH$_2$OC(O)CH=CH$_2$]$_2$ (IV)

A commercially available example of an epoxy acrylate oligomer is Novacure® 3600, and a commercially available acrylic acrylate polymer is Novacure® 6700, both of which are available from UCB Radcure, Atlanta, Ga.

The second essential component of the radiation-curable mixture used to form the controlled adhesion coating (B) is (B-2) at least one monomer selected from monofunctional acrylate monomers and polyfunctional acrylate monomers. In general these monomers are acrylated or methacrylated organic mono- and polyhydroxy compounds. These derivatives contain at least one acryloyl or methacryloyl group and preferably two acryloyl or methacryloyl groups in order to form a network upon polymerization (curing). These derivatives also function as reactive diluents for the oligomers. Suitable compounds include compounds represented by the general Formula V

R—(—C(O)—C(X)=CH$_2$)$_n$ (V)

wherein R is derived from a monohydroxy or polyhydroxy compound, X is hydrogen or a methyl or ethyl group, and n is an integer of at least 1. Preferably R is derived from a polyhydroxy compound, X is hydrogen or a methyl group, and n is 2, 3 or 4.

The acrylated organic mono- and polyhydroxy compounds (B-2) useful in the coating (B) and represented by the general Formula V may be prepared by techniques well known to those skilled in the art such as by the reaction of a hydroxy compound with acrylic acid, methacrylic acid or ethacrylic in mounts to provide the desired acrylated or polyacrylated product which is preferably a di-, tri-, or tetra-acrylated product. The molecular weights of the acrylated and methacrylated mono- and polyhydroxy monomers may be as high as 1200 and are generally below 1000. In one embodiment, the molecular weight of these monomers is between about 100 to about 1000. It is preferred that these acrylated and methacrylated mono- and polyhydroxy compounds are liquids which are not too viscous so that they can readily be blended with the oligomers (B-1) described above and may be used in part to reduce the viscosity of the mixture containing the oligomer. In general, these compounds may have viscosities at 25° C. at from about 2 to about 1000 cps., preferably from about 2 to about 500 cps., and more preferably between about 2 and 300 cps.

The acrylated and methacrylated monohydroxy compounds are generally derived from alcohols containing 6 or more carbon atoms, and these compounds are exemplified by hexyl acrylate 2-ethylhexyl acrylate (2EHA) hexyl methacrylate, octyl acrylate, decyl acrylate, decyl methacrylate, and mixtures thereof.

The polyfunctional compounds containing at least two hydroxyl groups may be monomeric polyhydroxy compounds such as ethylene glycol, diethylene glycol, 1,6-hexanediol, neopentylglycol, trimethylolpropane, pentaerythritol, etc. The polyfunctional compounds containing two or more hydroxyl groups also may be oligomeric compounds such as dimeric, trimeric or tetrameric polyhydroxy compounds.

Specific examples of acrylated and methacrylated organic polyhydroxy compounds include, for example, glycerol diacrylate, diethylene glycol diacrylate, 1,6-hexanediol diacrylate (HDODA), triethylene glycol diacrylate (TEGDA), trimethylol propane triacrylate (TMPTA), neopentyl glycol diacrylate, neopentyl glycol triacrylate, neopentyl glycol tetraacrylate, tripropylene glycol diacrylate (TRPGDA), 1,6-hexanediol dimethacrylate, ethylene glycol dimethacrylate, etc.

The radiation-curable mixtures which are used to form the controlled adhesion coating (B) generally comprise (i) from about 60% to about 95% by weight of at least one acrylated or methacrylated oligomer (B-1) and (ii) from about 5% to about 40% by weight of at least one acrylated organic mono- or polyhydroxy compound (B-2) as described above. In another embodiment, the radiation-curable mixtures used to form the controlled adhesion coating comprises (i) from 70% to about 95% of the acrylated or methacrylated oligomer (B-1), and (ii) from about 5% to about 30% by weight of at least one acrylated or methacrylated organic mono- or polyhydroxy compound (B-2).

When the radiation-curable acrylic mixture used to form the controlled adhesion coating is to be cured by exposure to non-ionizing radiation such as ultraviolet light, at least one photoinitiator is included in the curable composition in amounts of from about 0.5 to about 5% or even up to about 10% based on the total weight of the radiation-curable composition. Photoinitiators are not required when the radiation-curable composition is cured by electron beam radiation. Examples of photoinitiators which may be used in combination with ultraviolet light includes, for example, benzil ketals, benzoin ethers, acetophenone derivatives, ketoxime ethers, benzophenone, benzo or thioxanthones, etc. Specific examples of photoinitiators include: 2,2-diethoxyacetophenone; 2- or 3- or 4-bromoacetophenone; benzoin; benzophenone; benzoquinone; 1-chloroanthroquinone; p-diacetyl-benzene; 9,10-dibromoanthracene; 1,3-diphenyl-2-propanone; 1-hydroxycyclohexyl phenyl ketone, 1,4-naphthyl-phenyl ketone; 2,3-pentenedione; propiophenone; chlorothioxanthone; xanthone; and mixtures thereof.

The radiation-curable compositions used to form the controlled adhesion coating are prepared by mixing the above-described components. The components may be mixed at room temperature with stirring, and mild heating may be employed in some instances to facilitate mixing. Since the components of the composition may undergo some separation during storage, mild agitation or mixing just prior to use is effective to redisperse the components and is recommended.

The controlled adhesion coating (B) which is bonded to one surface of the polymeric backing sheet material (A) is obtained by applying the radiation-curable acrylic mixture to one surface of the backing sheet prior to curing. The acrylic mixtures may be applied to the backing sheet as a coating by any conventional means known in the coating art such as by roller coating, curtain coating, brushing, spraying, reverse roll coating, doctor knife, dipping, offset gravure, etc. In one particular embodiment, the liquid radiation-curable acrylic mixture is applied to the backing sheet using offset gravure techniques. The liquid being applied to the backing sheet may be heated or cooled to facilitate the coating process and to alter the depth of penetration of the liquid into the backing sheet prior to curing.

The amount of the radiation-curable mixture (B) applied to the one surface of the backing sheet (A) may be varied depending upon characteristics desired to be imparted to the substrate and the particular formulation of the curable mixture. If an excess of the coating composition is applied to the substrate, the physical characteristics of the substrates may be affected in an undesirable manner. Also, for economic reasons, it is normally desired to apply the lowest mount of coating to obtain the desired results. Typically, the applied coating weights may, depending on the substrate and intended use, range from about 0.02 to about 2.0 grams/m$^2$. More often, applied coating weights are from about 0.10 to about 1.5 or about 0.3 to 1.0 grams/m$^2$. At these levels, the coated backing sheet is characterized as having increased dimensional stability, increased strength, increased thermal stability increased resistance to solvents and moisture, and improved printability.

The backing sheets containing the controlled adhesion acrylic mixture as described above can be cured by exposure to known forms of ionizing or actinic non-ionizing radiation. Useful types of radiation include ultraviolet light, electron beam, x-ray, gamma-ray, beta-ray, etc. If ultraviolet light is to be used as the form of radiation, a photoinitiator such as described above is included in the curable release composition. Photoinitiators are not required for election beam curing. One of the advantages of using radiation to effect cure of the mixture is that polymerization takes place rapidly at ambient temperature, and heating is not necessary. The equipment for generating these forms of radiation are well known to those skilled in the art. Electron beam radiation is the presently preferred form of radiation to be used with the compositions of the present invention.

Curing of the controlled adhesion mixture can be effected in a continuous manner by passing the coated backing sheet through radiation equipment which is designed to provide the coated backing sheet with sufficient residence time to complete the cure of the coating. Curing may be effected in an air atmosphere or in an inert atmosphere such as nitrogen or argon. An inert atmosphere is preferred. The length of exposure necessary to cure the acrylic mixtures varies with such factors as the particular formulation used, type and wavelength of radiation, dosage rate, the atmosphere, energy flux, concentration of photoinitiator (when required), and thickness of the coating. Dosage rates of from 0.1 to about 10 megarads, generally below 4 megarads provide the desirable curing. Generally, the exposure is quite brief and curing is completed in less than about 0.1 to 3 seconds. The actual exposure time required to give proper curing for various coatings can be readily determined by one skilled in the art with a minimum of experimentation. Excess curing of the coatings generally should be avoided.

The following examples illustrate the compositions useful in preparing the controlled adhesion coatings useful in the present invention. Unless otherwise indicated in the following examples, in the specification, and in the appended claims, all parts and percentages are by weight, temperatures are in degrees centigrade, and pressures are at or near atmospheric pressure.

|  | %/Wt. |
| --- | --- |
| Example B-1 | |
| Novacure ® 7100 | 100 |
| Example B-2 | |
| Novacure ® 7100 | 90 |
| TMPTA | 10 |
| Example B-3 | |
| Novacure ® 7100 | 85 |
| TMPTA | 10 |
| HDODA | 5 |
| Example B-4 | |
| Novacure ® 7100 | 70 |
| TMPTA | 15 |
| HDODA | 15 |
| Example B-5 | |
| Novacure ® 3600 | 90 |
| TMPTA | 5 |
| HDODA | 5 |
| Example B-6 | |
| Novacure ® 6700 | 90 |
| TMPTA | 5 |
| HDODA | 5 |
| Example B-7 | |
| Novacure ® 7100 | 78 |
| TMPTA | 8 |
| HDODA | 8 |
| ODA (mixture of octyl & decylacrylates) | 6 |
| Example B-8 | |
| Novacure ® 7100 | 87 |
| ODA | 13 |

The reinforcing strips of the present invention may have a coating of adhesive (C) on the other surface of the polymeric backing sheet (A). The amount of adhesive applied to the surface of the polymeric backing sheet may range from about 5 to about 70 grams/m$^2$, and more often, the amount is in the range of about 10 to about 50 grams/m$^2$. Although any suitable adhesive may be used including hot melt and pressure-sensitive adhesives, in one preferred embodiment, the adhesive is a pressure-sensitive adhesive. Any adhesive may be used which forms an aggressive adhesive bond to the substrates to which the reinforcing strip is to be adhered. For example, it is desirable that the pressure-sensitive adhesive form an aggressive adhesive bond to the outer, liquid-impermeable film substrates used in disposable articles such as disposable diapers. The pressure-sensitive adhesive should be capable of holding the reinforcing strip tightly to the outer layer of, for example, a diaper, so that when the pressure-sensitive adhesive fastening tape tabs are applied to and adhere to the reinforcing strip, the tabs thereafter can be removed (peeled) from the reinforcing strip (e.g., on the diaper) without removing the reinforcing strip from its substrate (e.g., from the diaper).

Pressure-sensitive adhesive compositions are described in, for example, "Adhesion and Bonding", *Encyclopedia of Polymer Science and Engineering*, Vol. 1, pages 476–546, Interscience Publishers, 2nd Ed. 1985, the disclosure of which is hereby incorporated by reference. Such compositions generally contain an adhesive polymer such as natural, reclaimed or styrene butadiene rubber, tackified natural and synthetic rubbers, styrene butadiene or styrene isoprene block copolymers, random copolymers of ethylene and vinyl acetate, ethylene-vinyl-acrylic terpolymers, polyisobutylene, poly(vinyl ether), poly(acrylic) ester, etc., as a major constituent.

The block copolymers employed in the adhesive compositions may be thermoplastic block copolymers having linear, radial or star configurations and having the A blocks and B blocks formed into what are generally termed as ABA block copolymers. The A block is a monoalkenyl arene, mainly polystyrene, having a molecular weight between 4,000 and 50,000, preferably between 7,000 and 30,000. The A block content is from about 10% to 50%, more preferably between 10% and 30%. Other suitable A blocks may be formed from alpha-methyl styrene, t-butyl styrene and other ring alkylated styrenes as well as mixtures thereof. B is an elastomeric conjugated diene such as butadiene or isoprene having an average molecular weight of from about 5,000 to about 500,000, preferably from about 50,000 to 200,000. Preferably, ABA triblock and AB diblock copolymers will comprise the majority of the block copolymer elastomer of the adhesive, the percent diblock being less than 95% of the block copolymer, preferably less than 85%, and more preferably less than 75%. Other conventional diene elastomers may be used to a minor extent, but not so as to significantly effect the adhesion properties. The block copolymer is used in an amount ranging from about 30% to 60% by weight, preferably at 35% to 55% by weight of the adhesive composition.

Specific examples of ABA-type copolymers of styrene and isoprene are Kraton 1107 and Kraton 1117 from Shell Chemical Company. ABA-type copolymers of styrene-butadiene are available from Firestone under the designations Steron 840A and 845A. Other commercially available copolymer adhesives include: random copolymer of ethylene and vinyl acetate having a melt-flow index of 2500 in a vinyl acetate content of 14% by weight (Escorene MVO-2514), available from Exxon Chemical; styrene butadiene block synthetic rubber having a styrene content of 30% by weight (Finaprene 411), available from Fina Chemical Company; random copolymer of ethylene and vinyl acetate having a melt-flow index of 148 and a vinyl acetate content of 18.5% by weight (Elvax 420), available from DuPont; and random copolymer of ethylene and vinyl acetate having a melt-flow index of 57 and a vinyl acetate content of 40% by weight of an Elvax 40W.

Other materials may be included in the adhesive compositions such as solid tackifying resins, liquid tackifiers (often referred to as plasticizers), antioxidants, fillers, pigments, waxes, etc. The adhesive generally contains a blend of solid tackifying resin and liquid tackifying resin or liquid plasticizer.

The tackifying resins can be selected from the group of resins at least partially compatible with the B blocks of the elastomeric block copolymer materials of this invention. Such tackifying resins include those aliphatic hydrocarbon resins made from the polymerization of a feed stream consisting mainly of unsaturated species containing 4 to 6 carbon atoms; rosin esters and rosin acids; mixed aliphatic/aromatic tackifying resins; polyterpene tackifiers; and hydrogenated tackifying resins. The hydrogenated resins can include resins made from the polymerization and subsequent hydrogenation of a feedstock consisting mostly of dicyclopentadiene; resins produced from the polymerization and subsequent hydrogenation of pure aromatic feedstocks such as styrene, alphamethylstyrene, vinyl toluene; resins fashioned from the polymerization and subsequent hydrogenation of an unsaturated aromatic feedstream wherein the feedstream mainly contains species having from 7 to 10 carbon atoms; hydrogenated polyterpene resins; and hydrogenated aliphatic and aliphatic/aromatic resins. Preferred tackifying resins include the aliphatic hydrocarbon resins and the hydrogenated resins. Especially preferred are the aliphatic hydrocarbon resins. Specific examples include rosin acids, rosin esters, styrenated terpene resins, off-soluble phenolics, and polyterpenes. Commercially available tackifying resins include Escorez 1310 from Exxon Chemical Co., Wingtack Plus, Wingtack 10 and Wingtack 95 available from Goodyear Chemical Co., Hercolyn D from Hercules, Inc., and Zonarez A-25 from Anzona Chemical Co. The tackifying resin component can comprise the remainder of the functional adhesive composition, i.e., from 65% to 45% by weight. If a solid tackifier is employed, generally it will comprise from 25% to 60% by weight of the functional adhesive composition, preferably from 30% to 55% by weight. The liquid tackifying resin correspondingly would comprise 0–30% by weight of the functional adhesive composition, preferably from 5% to 20% by weight. Using the preferred level of solid and liquid tackifiers yields adhesives with a better balance of high peel adhesion values and shear adhesion values with good initial tack.

The liquid plasticizers suitable for use in the adhesive compositions of this invention include naphthenic oils, paraffinic oils, aromatic oils, and mineral oils. Preferred plasticizing liquids include naphthenic oils and slightly aromatic oils. The oils when used are preferably used in the same relative percentages as the liquid resins in combination with the solid tackifying resin.

The adhesive preferably is tackified with solid tackifying resin with liquid plasticizer and/or liquid resin of the above-described preferred types.

In one embodiment of the present invention, the adhesives may comprise from about 35–60% by weight of a synthetic thermoplastic block copolymer rubber as described above, about 30–60% by weight of at least one solid tackifying resin, 0 to about 20% by weight of a liquid tackifying resin, 0 to about 20% by weight of liquid extender oil, and a small amount of an antioxidant.

The following examples illustrate the types of adhesives which can be used in the present invention.

|  | Example C-1 |
|---|---|
| Kraton 1107 | 50 |
| Escorez 1310 | 30 |
| Wingtack 10 | 20 |
|  | Example C-2 |
| Kraton 1107 | 55 |
| Wingtack Plus | 40 |
| Wingtack 10 | 5 |
|  | Example C-3 |
| Kraton 1107 | 43 |
| Escorez 1310 | 37.5 |
| Zonarez A-25 | 18.5 |
| Irganox 1074 (antioxidant) | 1 |

The adhesive strips of the present invention may be prepared in sheet form and thereafter cut into strips of the desired dimensions. Alternatively, the adhesive strips can be prepared in a continuous manner from a roll of polymer backing material which may be in continuous strip or continuous sheet form, and if in sheet form, thereafter cut into a continuous strip of desired width. The order in which the controlled adhesion coating and the adhesive coating are applied to the polymer backing sheet is not critical. In one embodiment, the controlled adhesion coating composition is applied to one surface of the polymer backing sheet or strip and the adhesive is thereafter applied to the other surface of the polymer backing sheet or strip followed by curing of the controlled adhesion composition. In another embodiment, the controlled adhesion coating composition is applied to one surface of the polymer backing sheet or strip and cured. An adhesive is then applied to the other surface of the controlled-adhesion-coated backing sheet. The adhesive may be applied to the controlled adhesion-coated polymer backing sheet or strip soon after the controlled adhesion coating has been cured, or the adhesive can be applied at a much later time such as just prior to use.

One example of the adhesive strip of the present invention is illustrated in FIG. 1 which is an expanded perspective and cross-sectional view of a roll 18 of adhesive strip 10 of the invention. The strip 10 comprises a polymer backing sheet 12, a controlled adhesion coating 16 on the upper surface of the backing sheet 12, and a layer of adhesive 14 bonded to the lower surface of backing sheet 12. As mentioned above, the adhesive 14 may be, and preferably is, a pressure-sensitive adhesive. The adhesive strip can be wound into a roll 18 for storage and subsequent use, and the overlying portions of the strip do not become adhered together in storage as a result of the presence of the controlled-adhesion coating on the upper surface of the strip. Thus, the strip can be unwound with minimum difficulty after storage. Prior to unwinding the roll, the roll can be cut to form supply rolls of the desired width such as widths of 4 to 8 or 10 inches.

FIG. 1 also shows adhesive strip 10 as it might be formed into a roll of the strip wound directly upon itself. The strip is wound so that the adhesive layer 14 is on the inside. In the roll 18, the substrate 12 and coating 16 not only serve as a base or support for the adhesive coating, but also as a temporary liner. In each turn of the roll, the controlled adhesion coating 16 temporarily contacts and covers the adhesive surface of the overlying min. The controlled and low adhesion between the coating 16 and the pressure-sensitive adhesive 14 makes it possible to unwind the tape with a minimum of effort, and when the tape is unwound, there is less pull on the adhesive when it is separated from the roll thereby reducing the forces which could otherwise cause delamination of the tape structure and/or tearing of the tape. The degree of adhesion between the adhesive layer 14 and the coating 16 in the roll is sufficient to maintain the wound tape in place and prevent spontaneous separation of the turns of the roll.

In one example of the process whereby a self-wound roll of controlled-adhesion tape is manufactured, a long sheet of polyethylene in roll form is unwound, drawn through a gravure coater which applies the uncured (i.e., liquid) controlled-adhesion coating to one side thereof. The coated polyethylene sheet is passed through a chamber wherein it is subjected to a source of (ionizing or nonionizing) radiation which cures the liquid coating. The inside of the chamber through which the sheet passes may be inerted with non-oxygen-containing gas such as nitrogen or argon so as to prevent premature cessation of the curing process and thereby promote more thorough curing of the coating. The long sheet is then drawn out of the curing chamber and through a (slot die) hot melt adhesive applicator which coats the non-controlled-adhesion side of the sheet with a (continuous or patterned) layer of normally tacky pressure-sensitive adhesive. The coatweight of the adhesive is ordinarily between 10 and 50 grams per square meter. After adhesive application, the long coated sheet is rewound into the form of a self-wound roll with the adhesive-coated side wound inward. In a separate operation the large roll of self-wound tape may be slit into a multiplicity of smaller and more narrow rolls.

The following examples illustrate the controlled adhesive strips of the present invention.

EXAMPLE A (A) Backing sheet: polyethylene
(B) Controlled adhesion coating: Example B-5
(C) Adhesive: Styrene-butadiene copolymer

EXAMPLE B (A) Backing sheet: biaxially oriented polypropylene film
(B) Controlled adhesion coating: Example B-3
(C) Adhesive: a styrene-isoprene copolymer block-type adhesive (Example C-2)

The adhesive strips of the present invention are useful in particular as target strips to reinforce and strengthen specific areas or portions of articles and garments such as disposable diapers which utilize fastening tapes containing pressure-sensitive adhesives.

In one embodiment, an article of the present invention comprises (A) a liquid-impermeable film substrate;

(B) a peel-resistant target strip having one surface thereof bonded to the film substrate, and on the other surface, a controlled adhesion coating of a radiation-cured mixture comprising (B-1) a major amount of at least one oligomer selected from amine acrylate oligomers, epoxy acrylate oligomers, urethane acrylate oligomers, and acrylic acrylate oligomers, and (B-2) a minor amount of at least one monomer selected from monofunctional acrylate monomers and polyfunctional acrylate monomers; and (C) at least one pressure-sensitive adhesive fastening tape tab attached to the film substrate (A) in an area of the substrate removed from the target strip whereby the fastening tape tab may be adhered to the target strip to hold the article in a desired position by hand-pressure and may be removed and reapplied without distortion or tearing of the strip or the liquid-impermeable film substrate.

The liquid-impermeable film substrate (A) of the article may be any liquid-impermeable film substrate. When the substrate is a disposable diaper, the film substrate is the outer layer of the disposable diaper which generally will be a thermoplastic polymer film such as polyolefin films, polyester films, etc., preferably with a matte or embossed surface. Polyethylenes and polypropylene are examples of polyolefins that can be used to prepare the liquid-impermeable films.

The peel-resistant target strip which is present in the article comprises a polymer backing sheet having one surface thereof bonded to the film substrate, and the other surface coated with a controlled adhesion coating of the radiation-cured mixtures described above. The target strip may be bonded to the film substrate by any means known to those skilled in the art such as with adhesives. In a preferred embodiment, the adhesive strip of the present invention which has been described in detail above is utilized as the target strip. In this embodiment, the adhesive strip is cut to the desired dimensions and applied to the film substrate with heat or pressure. In those instances where the adhesive on the adhesive strip is protected with a releasable liner, the liner is removed, and the adhesive side of the strip is brought into contact with the film substrate and bonded thereto. The target strip defines an area (often referred to as "landing zone") of reinforced strength which provides a target or landing for the adhesive fastening tape tabs used to close or shape various articles such as diapers and forms a secure closure. The fastening tape tabs can be repeatedly peeled from the target strips without distorting or tearing the target strip or the liquid-impermeable film substrate of the article.

In one preferred embodiment, the articles of the present invention comprise disposable garments such as disposable diapers wherein the adhesive strips of the present invention are used to reinforce selected areas. In particular, the adhesive strips are applied to the selected portions of the outer shell to serve as target strips or landing zones for receiving the adhesive fastening tape tabs. The adhesive strips become bonded to the liquid-impermeable film of the outer layer of the diaper in a peel-resistant manner such that the fastening tape tabs may strongly adhere to the target strips by simple hand-pressure, and the adhesion between the fastening strip tabs and the target area maintained for an extended period. However, the adhesion between the fastening tape and the target strip is not so great that the fastening tape tabs cannot be removed and reapplied without distortion or tearing of the liquid-impermeable film or the target strip.

Figure 2:
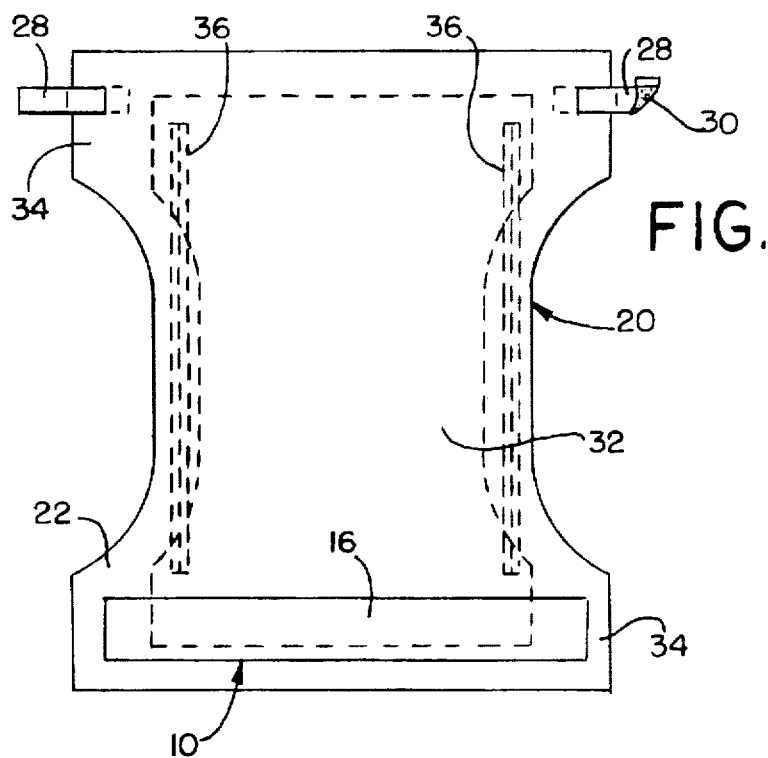
FIG. 2 is a top view of a disposable diaper in accordance with the invention.
Figure 3:
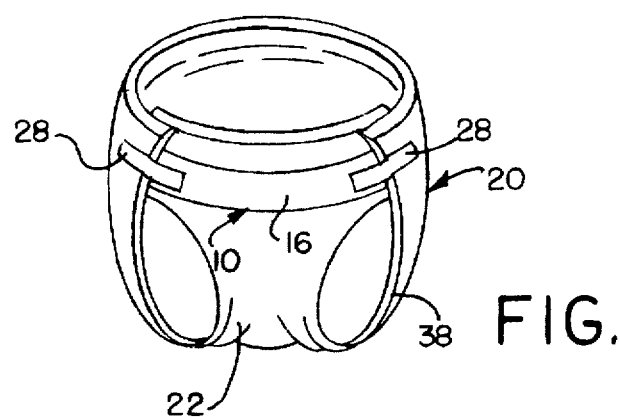
FIG. 3 is a view of the disposable diaper of FIG. 2 in closed position.

The utility of the adhesive reinforcing strips of the present invention in disposable articles such as diapers is illustrated in FIGS. 2 and 3. FIG. 2 illustrates a disposable diaper of the invention 20 having a generally "hour-glass" or I-shape with a central narrowed crotch section 32 and waistband sections 34. The diaper is shown laid flat with the outer water-impermeable layer 22 facing up. A target strip 10 is shown attached to the outer layer 22. The diaper 20 also contains pressure-sensitive adhesive fastening tape tabs 28 with pressure-sensitive adhesive 30 which are used to fit the diapers to the wearer by adhering tabs 30 to the controlled adhesion coating 16 of target strip 10. The diaper illustrated in FIG. 2 also contains elastic means 36 which are typically secured in place adjacent to the absorbent batt on each side thereof to develop gathered elastic leg portions 38 which are comfortable when in contact with an infant's legs (FIG. 3).

FIG. 3 is a view of the diaper 20 of FIG. 2 in a closed position in which the pressure-sensitive adhesive fastening tape tabs 28 are adhered to the controlled adhesion coating 16 on the target strip 10 which is adhered to the outer layer 22 of the diaper.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A disposable diaper comprising (A) a liquid-impermeable film substrate;

(B) a peel-resistant target strip comprising a polymeric backing sheet material having one surface thereof bonded to the film substrate, and on the other surface, a coating of a radiation-cured mixture comprising (B-1) from 60% to 95% by weight of an amine acrylate oligomer having a molecular weight of up to about 2000, (B-2) from 5% to 40% by weight of at least one acrylated or methacrylated organic polyhydroxy compound, and (C) at least one pressure-sensitive adhesive fastening tape attached to the film substrate in an area of the film substrate removed from the target strip whereby a free end of the fastening tape may be adhered to the target strip by hand pressure to hold the diaper in a desired position, and the fastening tape may be removed and reapplied without distortion or tearing of the liquid-impermeable film substrate.

2. The disposable diaper of claim 1 wherein the target strip is bonded to the film substrate with a pressure-sensitive adhesive.

3. The diaper of claim 1 wherein the target strip comprises a polymeric backing sheet material having an adhesive on one surface thereof adhered to the film substrate, and the controlled adhesion coating on the other surface.

4. The diaper of claim 1 wherein the backing sheet material is formed from a thermoplastic material.

5. The diaper of claim 1 wherein the backing sheet material is formed from a thermoplastic material selected from the group consisting of polyesters and polyolefins.

6. The diaper of claim 1 wherein the backing sheet material is a polyolefin selected from the group consisting of polypropylene, polyethylene, and mixtures of polyethylene and polypropylene.

7. The diaper of claim 1 wherein the controlled adhesion coating comprises a radiation cured mixture comprising
- (B-1) from 70% to 95% by weight of an amine acrylate oligomer, and
- (B-2) from 5% to 30% by weight of at least one acrylated or methacrylated organic polyhydroxy monomer.

8. A disposable diaper comprising
- (A) a liquid-impermeable film substrate;
- (B) a peel-resistant target strip having one surface thereof bonded to the film substrate, and on the other surface, a coating of a radiation-cured mixture comprising
  - (B-1) from 70% to 95% by weight of at least one oligomer selected from amine acrylate oligomers, epoxy acrylate oligomers, and acrylic acrylate oligomers, and
  - (B-2) from 5% to 30% by weight of at least one monomer selected from monofunctional acrylate monomers and polyfunctional acrylate monomers; and
- (C) at least one pressure-sensitive adhesive fastening tape attached to the film substrate in an area of the film substrate removed from the target strip whereby the fastening tape may be adhered to the target strip to hold the article in a desired position by hand-pressure and may be removed and reapplied without distortion or tearing of the strip or the liquid-impermeable film substrate.

9. The diaper of claim 8 wherein the target strip comprises a polymeric backing sheet material having an adhesive on one surface thereof adhered to the film substrate, and the controlled adhesion coating on the other surface.

10. The diaper of claim 8 wherein said liquid-impermeable film substrate is formed from a thermoplastic material.

11. The diaper of claim 8 wherein said liquid-impermeable film substrate is formed from a thermoplastic material selected from the group consisting of polyesters and polyolefins.

12. The diaper of claim 8 wherein said liquid-impermeable film substrate is a polyolefin selected from the group consisting of polypropylene, polyethylene, and mixtures of polyethylene and polypropylene.

13. The diaper of claim 8 wherein the controlled adhesion coating comprises a radiation cured mixture comprising
- (B-1) from 70% to 95% by weight of an amine acrylate oligomer, and
- (B-2) from 5% to 30% by weight of at least one acrylated or methacrylated organic polyhydroxy monomer.

14. The diaper of claim 8 wherein the oligomer of (B-1) has a molecular weight of up to 2000.

* * * * *